United States Patent [19]
Torrey et al.

[11] Patent Number: 5,440,360
[45] Date of Patent: Aug. 8, 1995

[54] REFLECTIVE STIMULUS FOR COMPUTER SCREEN SIMULATION FOR EYE EXAMINATIONS

[75] Inventors: Jonathan G. Torrey; Cosmo Salibello, both of Portland, Oreg.

[73] Assignee: Prio Corporation, Lake Oswego, Oreg.

[21] Appl. No.: 148,693

[22] Filed: Nov. 5, 1993

Related U.S. Application Data

[63] Continuation-in-part of Ser. No. 211, Jan. 4, 1993, Pat. No. 5,325,136, which is a continuation-in-part of Ser. No. 665,903, Mar. 7, 1991, Pat. No. 5,191,367, which is a continuation-in-part of Ser. No. 282,596, Dec. 12, 1988, Pat. No. 4,998,820.

[51] Int. Cl.$^6$ .......................... A61B 3/032; A61B 3/02
[52] U.S. Cl. .................... 351/239; 351/222; 351/246
[58] Field of Search ............ 351/200, 222, 239, 243, 351/244, 246, 203

[56] References Cited

U.S. PATENT DOCUMENTS

| | | | |
|---|---|---|---|
| 2,180,652 | 11/1939 | Wilson | 351/237 |
| 2,282,494 | 5/1942 | Potter | 351/233 |
| 2,853,919 | 9/1958 | Richards | 351/246 |
| 4,212,520 | 7/1980 | Klimsa | 351/243 |
| 4,365,873 | 12/1982 | Ginsburg | 351/239 |
| 4,421,392 | 12/1983 | Pitts Crick et al. | 351/224 |
| 4,550,990 | 11/1985 | Trispel et al. | 351/243 |
| 4,572,630 | 2/1986 | Task et al. | 351/243 |
| 4,576,454 | 3/1986 | Charney et al. | 351/243 |
| 4,611,893 | 9/1986 | Schrier | 351/239 |
| 4,615,594 | 10/1986 | Task | 351/243 |
| 4,764,007 | 8/1988 | Task | 351/243 |
| 5,191,367 | 3/1993 | Salibello et al. | 351/243 |

*Primary Examiner*—William L. Sikes
*Assistant Examiner*—David R. Parsons
*Attorney, Agent, or Firm*—Marger, Johnson, McCollom & Stolowitz

[57] ABSTRACT

A test card for use in eye examinations emulates the light return profile of a video display screen such as those commonly used in connection with computers. The test card is used for prescribing corrective lenses for a computer user. The test card is formed on an opaque planar medium and has a plurality of characters formed thereon for reading by the patient, each character formed by a plurality of pixel elements. The pixel elements may be formed by designing a pattern of dots on a computer system using graphic software for representing the resulting pattern in a machine-readable graphics file. The graphics file is used to control a compatible imagesetter machine for forming the desired pattern on photographic film. According to an alternative method, a film master is prepared in which each pixel is a solid black dot. The test card is prepared by printing the image onto photographic paper through a diffusion element so as to create an approximately Gaussian light return profile across each pixel.

11 Claims, 8 Drawing Sheets

REFLECTIVE STIMULUS FOR COMPUTER SCREEN SIMULATION FOR EYE EXAMINATIONS

RELATED APPLICATION DATA

This application is a continuation-in-part of application Ser. No. 8/000,211 filed Jan. 4, 1993, now U.S. Pat. No. 5,325,136 which is a continuation-in-part of application Ser. No. 07/665,903, filed Mar. 7, 1991, now U.S. Pat. No. 5,191,367 which is a continuation-in-part of application Ser. No. 07/282,596, filed Dec. 12, 1988, now U.S. Pat. No. 4,998,820.

FIELD OF THE INVENTION

The present invention relates to vision testing equipment and, more specifically, to a test card for use in conducting optometric examinations, and to methods of making such apparatus.

BACKGROUND OF THE INVENTION

As use of the video display terminal ("VDT") has become more widespread, for example in connection with computers, so too have certain ophthalmological problems associated with its use become more common. A recent survey of optometrists, reported in the J. Am. Optom. Assoc. 1992 (vol. 63, pp 687–92), shows that more than 14% of optometric patients present with symptoms primarily associated with use of the VDT, or almost 10 million examinations annually when projected to the U.S. population. Responding optometrists were unable to confidently arrive at a diagnosis and treatment more frequently for VDT patients (20.87%) compared to non-VDT patients (14.05%).

Alphanumeric characters displayed on video display screens are made up of dots or "pixels" which do not have well-defined edges and therefore are difficult for the eye to focus upon. Further, since video screens are maintained at a constant distance of about 50 cm from the user's eyes, the same eye muscles are in constant use in focusing on the screens. These factors cause significant amounts of stress and fatigue on the eyes of VDT users which are often aggravated by the fact that many such users utilize their computers for extended periods on a daily basis. The stress associated with video display use frequently results in peculiar types of eye problems requiring special corrective prescriptions in the spectacles selected for the users suffering from these problems.

In order to accurately diagnose these problems, appropriate test equipment and test procedures must be provided. In accordance with the process currently used by medical practitioners to determine the spectacle requirements of typical patients, an apparatus (phoropter) is placed in front of the eyes of the patient which enables the doctor to rapidly change a wide selection of lenses while the patient views a set of test images through the lens changing apparatus. As the patient focuses on the test images, the doctor assesses the status of the muscles inside the patient's eyes and judges their degree of relaxation through the use of a retinoscope. The doctor determines the combination of lenses and the prescription best suited to the patient by changing the lenses until he detects the combination which provides the most relaxed state in the eye muscles of the patient.

As may be understood from the above, the fitting of corrective lenses is basically a trial and error process in which the doctor observes the reaction of the patient's eye muscles to an appropriate test image for various combinations of lenses. However, without a test image which accurately simulates the conditions under which the patient may experience eye problems, a prescription for suitable corrective lenses may not be reliably determined. When presented with an image which does not have sharply defined edges or which is slightly out of focus, the eye will respond by reverting to a level of tonic muscle activity known as the resting point of accommodation, having a focal length with a sharply defined image placed at the same distance from the eye. Accordingly, the prescription required for eyeglasses used with a video display terminal can differ frown a prescription for use in viewing printed material.

A vision tester apparatus is disclosed in commonly-owned U.S. Pat. No. 5,191,367. That apparatus, although quite useful for its intended purpose—computer screen simulation for optometric examinations—is costly to manufacture. It also is susceptible to various mechanical or electrical failures. The need remains, therefore, for providing eye care practitioners with equipment for VDT-user examinations that is inexpensive, reliable and easy to maintain.

SUMMARY OF THE INVENTION

One aspect of the present invention is an optometric test card for reading by a patient during an eye examination. The test card preferably comprises an opaque, generally planar medium such as stiff photographic paper. A plurality of characters such as alphanumeric characters are formed thereon for reading by the patient. Each character is formed by a plurality of pixel elements or "dots" arranged in a predetermined pattern. Each pixel element exhibits a maximum density adjacent its center, and the density gradually decreasing as a function of distance from the center so that the edges of the pixel elements are "soft" or blurred. The dots are sized so that individual dots are not discernable by the patient at a viewing distance greater than approximately 15 inches. As a result, the characters appear fuzzy to the patient, thereby simulating the visual characteristics of a typical computer display screen. The test card may include an aperture extending therethough, the aperture sized and arranged so as to allow an examiner to view the patient's eyes generally along the patient's line of sight by looking through the test card from a side of the test card opposite the patient while the patient reads the characters on the test card.

Another aspect of the invention is a method of making the test card described. The method includes selecting a plurality of symbols or characters for viewing by a patient and forming an image of the selected symbols on a single substantially opaque substrate for presentation to the patient. Preferably, the step of forming the image includes reducing a density of each symbol along its peripheral edges relative to a maximum density within the corresponding symbol, so that the edges of the symbols will appear fuzzy to the patient, thereby stimulating the visual effect of a computer display screen for the purpose of an optometric examination.

The effect of reducing the density along the edges of the symbols is achieved by forming each symbol out of a plurality of pixel elements. Each pixel element is formed of a plurality of dots, arranged in a predetermined pattern having a maximum dot density per unit area adjacent the center of the pattern, the dot density gradually decreasing as a function of distance from the center. The dots are sized so that individual dots would not be discernable by a patient at a viewing distance greater than approximately 15 inches (38 cm.), a typical viewing distance for a computer screen display. The test card may be economically produced in volume using known photographic processes.

The foregoing and other objects, features and advantages of the invention will become more readily apparent from the following detailed description of a preferred embodiment which proceeds with reference to the drawings.

DETAILED DESCRIPTION OF THE PREFERRED EMBODIMENT

Figure 1:
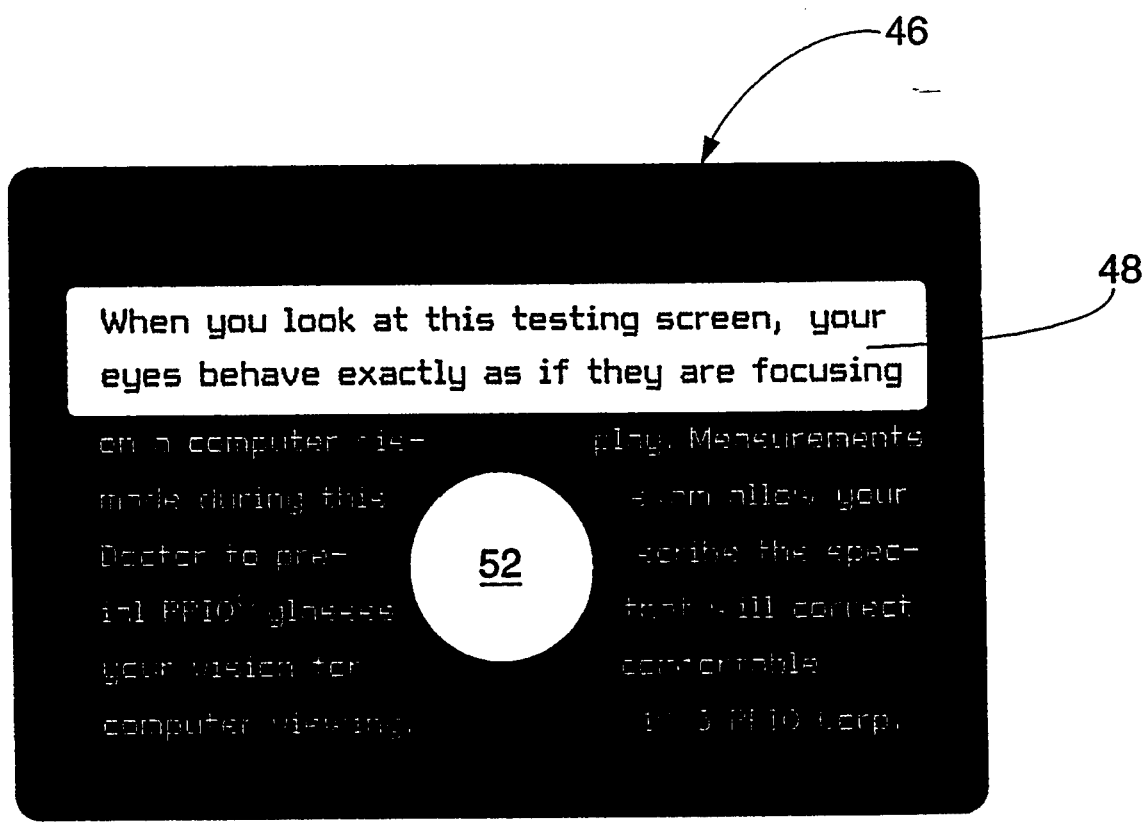
FIG. 1 is a front view of a test card according to the present invention.
Figure 2:
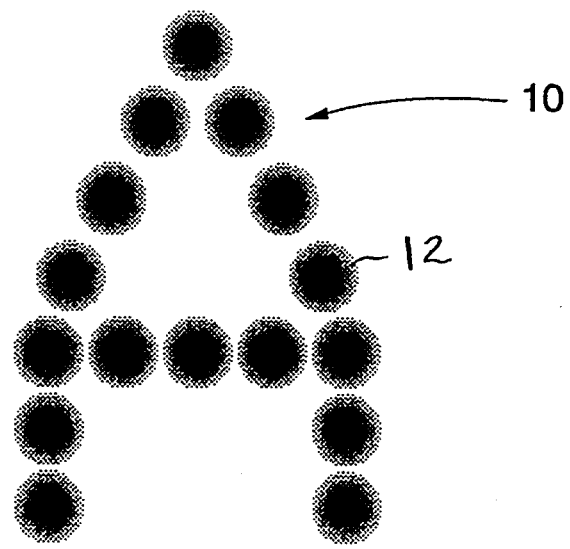
FIG. 2 is an enlarged view of a portion of the test card of FIG. 1.

An optometric test card 46 is illustrated in front view in FIG. 1. The test card image is formed from an opaque, generally planar medium such as stiff photographic paper. An aperture 52 extending through the test card may be provided. The aperture is sized and arranged so as to allow an Examiner to view the patient's eyes generally along the patient's line of sight by looking through the test card from a side of the test card opposite the patient (the back side) while the patient reads the characters formed on the test card. FIG. 2 is an enlarged view of one of the characters ("A") formed on the test card of FIG. 1. This shows how each character 10 is formed of a plurality of pixel elements 12 arranged in a predetermined pattern so as to form the desired character. Each pixel element has a maximum density adjacent its center, and the density gradually decreases as a function of distance from the center, so that the edges of the characters appear fuzzy to the patient. This effect simulates the output of a typical computer display screen.

Figure 3:
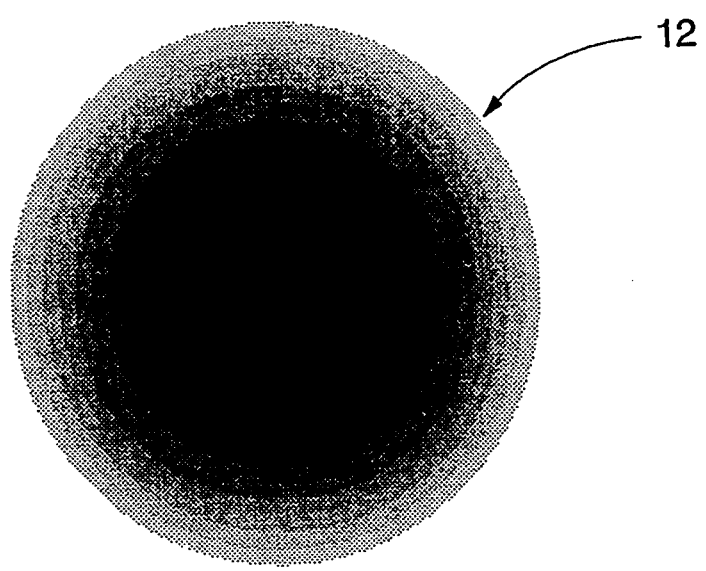
FIG. 3 is a further enlarged view of an individual pixel element of the test card of FIG. 1 to illustrate gradations in optical density.
Figure 4:
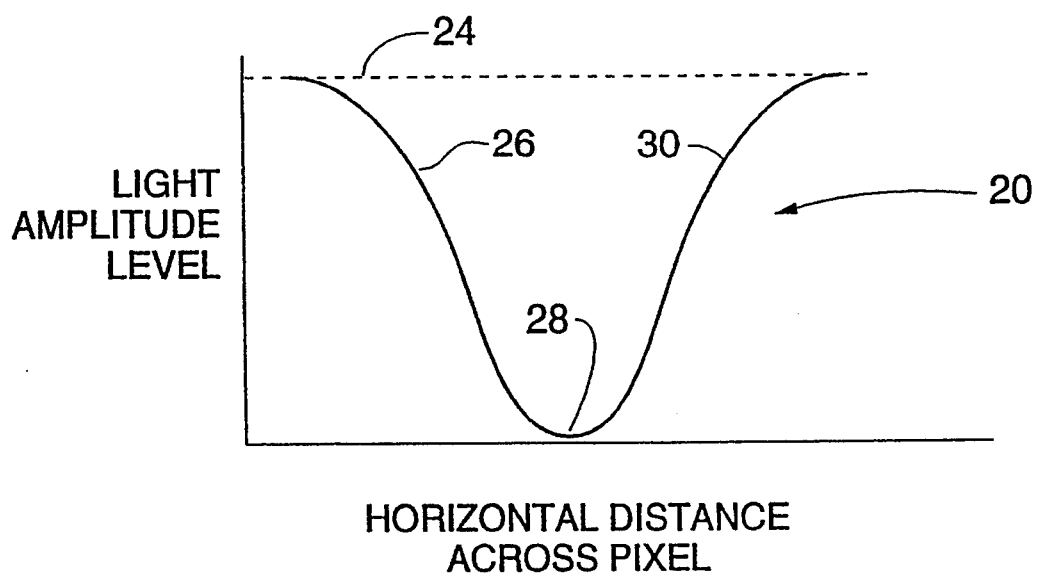
FIG. 4 is graph representing light amplitude level as an approximately Gaussian function of distance across a diameter of the pixel element of FIG. 3.

In particular, the density of each pixel element 12 is an approximately Gaussian function of distance from the center of the pixel element. FIG. 3 is a further enlarged view of an individual pixel element 12 of the test card of FIG. 1 to more clearly illustrate gradations in optical density. In FIG. 4, a plot 20 shows light amplitude level versus horizontal distance across the pixel of FIG. 3. It may be observed that the light amplitude level gradually decreases from an initial or ambient level indicated by dashed line 24, along an inverted bell curve to a cusp or minimum 28 corresponding to the center of pixel 12 where the density is at a maximum (black). Continuing horizontally across the pixel, the light amplitude level then gradually increases along curve 30 till it reaches the, maximum level 24. The pixel element 12 and the light amplitude plot 20 preferably are symmetric. The light amplitude curve 20 is somewhat idealized or smoothed in that the pixel element actually comprises a series of discrete concentric bans, each having a different density. Accordingly, a more exact plot of light amplitude level would exhibit a staircase effect showing a step change in light amplitude level at the transition between each of the concentric bans, although the overall inverted bell shape of the curve is accurate. This light amplitude characteristic is selected to most closely emulate the pixels of a computer display screen in which light is transmitted from a point source.

A practical method of making a test card of the type described calls for using a plurality of discrete dots clustered together so as to form each pixel element. Thus, each pixel element comprises an array of dots having a center, in which the density of discrete dots is maximized adjacent the center of the array and the dot density gradually decreases as a function of distance from the center of the array, as further explained below. The dots are sized so that individual dots are not discernible by a patient at a viewing distance greater than an approximately 15 inches (38 cm), a typical computer display screen viewing distance. Since the individual dots are not discernible, the array or cluster simulates an individual pixel of a computer display screen.

Figure 5:
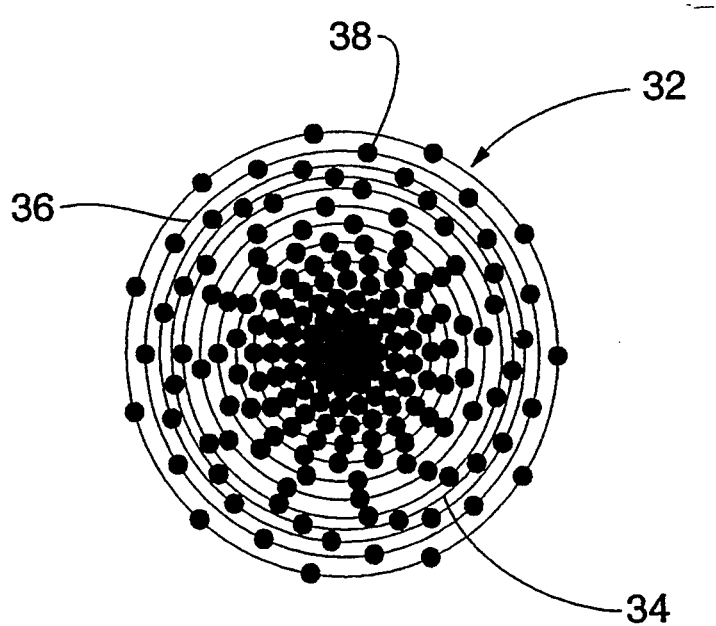
FIG. 5 illustrates an array of black dots arranged to form a pixel element.

Referring now to FIG. 5, a preferred array of dots 32 is illustrated. Each individual dot (for example dot 38) is disposed on one of a series of concentric circular rings (for example rings 34, 36). This arrangement is convenient for creating a cluster of dots having the desired density distribution. Each individual dot is substantially circular and has a diameter on the order of 0.001 inch (0.025 mm). These dimensions are far too small to carry out the method manually. Two methods of creating the test cards are disclosed herein, the imagesetter method and the diffusion method. The imagesetter method involves the use of a computer and suitable software for generating film work masters on a machine that converts electronic layout files to photographic film. The electronic file that provides an original image for this method may be created, for example, in a software program called "Adobe Illustrator", made by Adobe Systems, Inc. Release version 3.2.3 was used in the examples discussed herein. Using the computer, each pixel element is formed of a cluster or group of black circular dots, on the order of 0.001 inch in diameter. The dots are arranged in concentric circles, with the spacing of dots increasing as a function of distance from the center. In one example of a preferred embodiment, the center of the pixel is coincident with the center point of the first dot. Next, six 0.001 inch dots are positioned with their centers spaced apart at 60° angles on a circle of 0.0019 diameter having its center at the center of the pixel. Continuing outward, twelve dots are placed with their centers spaced 30° on a circle of 0.0038 inch diameter. The placements of dots continues as shown in the following table.

| Centerline Circle Dia. | Number of Dots on Circle |
| --- | --- |
| .0057" | 18 |
| .0076" | 19 |
| .0095" | 20 |
| .0113" | 19 |
| .0133" | 15 |
| .0151" | 12 |
| .0171" | 11 |
| .0180" | 11 |
| .0183" | 11 |
| .0210" | 11 |

Figure 6:
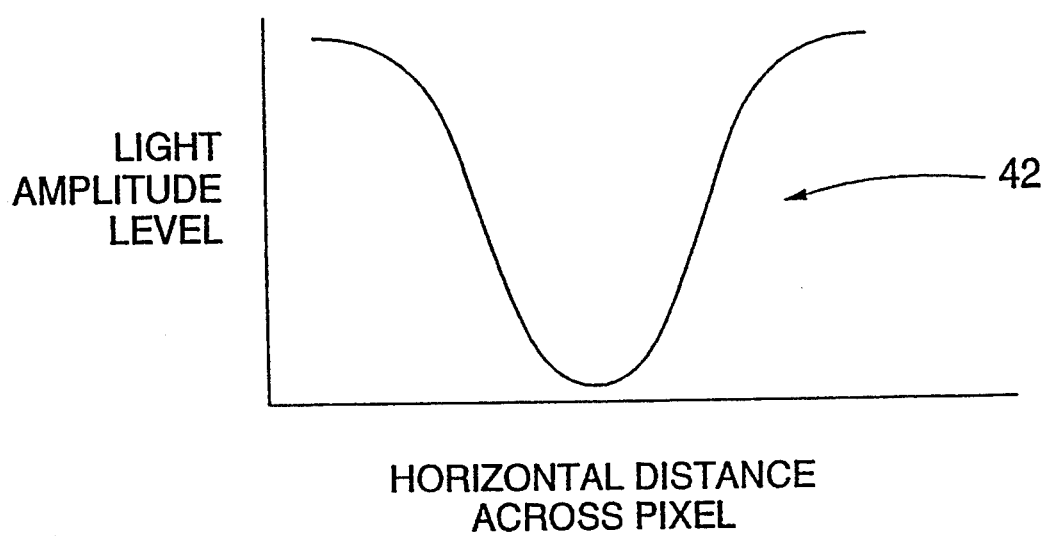
FIG. 6 is graph representing light amplitude level as an approximately Gaussian function of distance across the pixel element of FIG. 5.

This arrangement is illustrated in FIG. 5. A cluster of dots formed according to this arrangement exhibits a light amplitude level as a function of horizontal distance as indicated by the curve 42 in FIG. 6. The electronic file thus created is converted to photographic film by an imagesetter machine using, for example PostScript ® page description language. In the operative example, the imagesetter used was a ColorSetter ®, manufactured by Optronics Corporation. The output film is 0.007" Kodak negative photographic film, with the emulsion layer right-reading on the rear surface. This provides a master film image. Production duplicates of the master are created by standard photographic contact duplication, using Kodak QCP resin-coated negative photographic paper or a similar product. This results in production images having black characters on a white background. The same characters can be created using Kodak QCP resin-coated positive photographic paper, to result in production images with white characters on a black background. The black characters on the white background are shown as panel 48 in FIG. 1.

The concentric circles, for example circles 34, 36, merely illustrate the placement of the individual dots. The circles themselves are not part of the image. The arrangement of the dots described exhibits the desired Gaussian light amplitude levels, and is reasonably uniform at the viewing distances of interest.

The production images produced on photographic paper may be mounted to a substrate of stiffer material. The test card, thus reinforced, may be mounted to a bracket and suspended from a typical ophthalmic chair reading rod.

The overall effect of the preceding arrangement of dots into pixels is seen when viewed from a distance on the order of 20". The viewer's eye cannot resolve the individual dots, and the pixels are perceived as having poorly-defined or fuzzy edges. This acts to drive the viewer's focus to their resting point of accommodation, which can be measured by the eye care practitioner. The test card apparatus and method of the invention thus provide a simple and inexpensive means for simulating computer display screens for ophthalmic examination.

Diffusion Method

An alternative method of making a test card that involves the use of the same computer hardware and software described above, and the step of generating a film work master on an imagesetter. However, according to the alternative method, the film work master consists of a square-wave image, with the Gaussian characteristics imparted during the process of duplication onto photographic paper.

Figure 9:
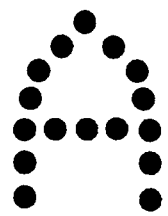
FIG. 9 illustrates a portion of an image master showing a character formed of a plurality of dots prior to diffusion printing.

In one example of an operative embodiment, to generate the diffusion master, the Adobe Illustrator ® computer program is used to locate 0.003" diameter dots arranged in predetermined patterns in a 7×9 matrix so as to create desired alphanumeric characters. These dots are spaced approximately 0.012" to 0.015" on center, similar to the spacing preferred for the pixel method described above. However, in this case the dots are solid black, as distinguished from the fuzzy pixel elements 12 of FIG. 2. FIG. 9 illustrates the solid dots arranged as described so as to form the letter "A". Such characters may be arranged into words and sentences as illustrated in FIG. 1. Arrangement of the characters into actual readable text is preferred so that the patient actually reads the test card, just as the patient in practice actually reads the text on a computer display screen.

Next, the electronic file provided by the Adobe Illustrator ® is convened into photographic film by an Optronics imagesetter using PostScript ® page description language, as noted above. The output film again may be 0.007" Kodak negative photographic film, with the emulsion layer right-reading on the rear surface. This provides a master film image. Note, however, that in this case larger (0.003" diameter) dots are used in lieu of the clusters of smaller dots described above for forming a pixel element.

Production duplicates of this master image are created by standard photographic contact duplication, but with the addition of a spacer layer introduced between the emulsion layer of the film master and the front surface of the Kodak QCP resin-coated negative photographic paper.

Figure 7:
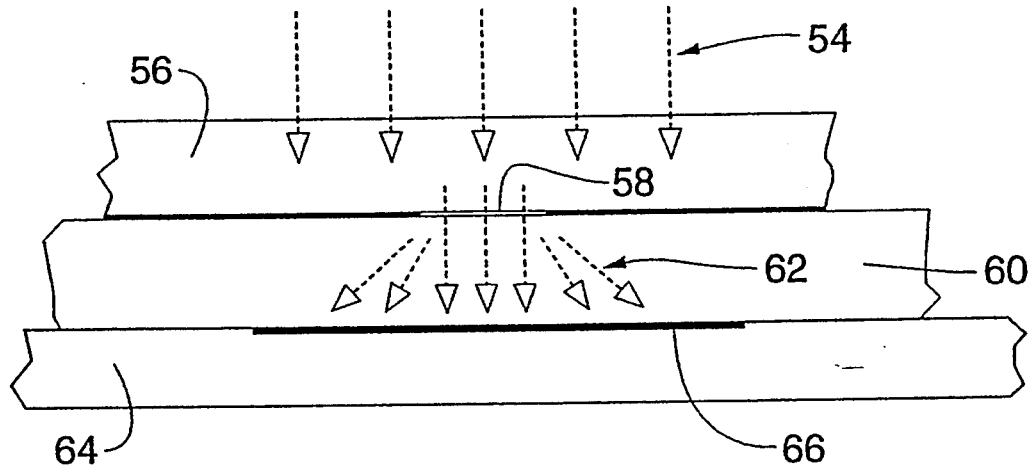
FIG. 7 is a cross-sectional view of an arrangement of materials for forming an image on a photo-sensitive medium according to the present invention.
Figure 8:
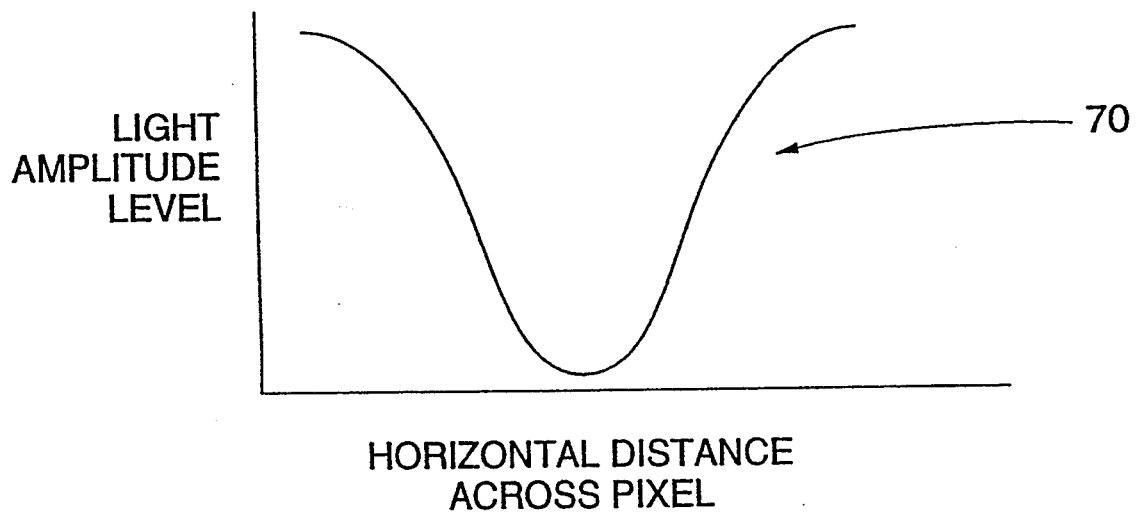
FIG. 8 is graph representing light amplitude level as an approximately Gaussian function of distance across a pixel element formed on a photographic paper using one method of the present invention.

Referring to FIG. 7, a cross-sectional view is shown of an apparatus for forming an image on a photo-sensitive medium according to this diffusion method. In the figure, light energy indicated by dashed arrows 54 is directed through the photographic negative film master 56. Each individual dot on the master results in a 0.003" diameter opening, for example opening 58 in the emulsion layer of the film master. Accordingly, light energy indicated by dashed arrows 62 is transmitted through the opening and dispersed in the diffusion layer 60. The diffusion layer preferably is formed of a polyester spacer, on the order of 0.011" thick. A sheet of resin-coated negative photographic paper 64 is positioned in parallel contact with a side of the polyester spacer opposite the film master. The spacer disperses the light, as indicated by dashed arrows 62. As a result, a solid black dot in the master image that formed opening 58 in the film creates a corresponding diffused image 66 on the surface of the photographic paper 64. Because of the diffusion employed, image 66 will have a maximum density at its center, so that light amplitude level is at a minimum, and the light amplitude will vary as a function of horizontal distance across the image in a substantially Gaussian function as illustrated by curve 70 in FIG. 8. The resulting photographic paper may be mounted to a stiffer substrate as described above.

Having illustrated and described the principles of my invention in a preferred embodiment thereof, it should be readily apparent to those skilled in the art that the invention can be modified in arrangement and detail without departing from such principles. We claim all modifications coming within the spirit and scope of the accompanying claims.

We claim:

1. An optometric test card for reading by a patient during an eye examination comprising:

an opaque, generally planar medium having a plurality of characters formed thereon for reading by the patient, each character formed by a plurality of pixel elements arranged in a predetermined pattern:

each pixel element comprising an array of dots having a center, the array having a maximum density of dots adjacent the center of the array and the dot density gradually decreasing as a function of distance from the center; and the dots being sized so that individual dots are not discernable by the patient at a viewing distance greater than approximately 15 inches (38 cm.) so that the edges of the characters appear fuzzy to the patient, thereby simulating the visual effect of a computer display screen.

2. A test card according to claim 1 wherein each array of dots is generally circular.

3. A test card according to claim 1 wherein the medium is light colored and the dots are substantially black.

4. A test card according to claim 1 wherein the dots are substantially circular and each has a diameter on the order of 0.001 inch (0.025 mm).

5. A test card according to claim 1 wherein the planar medium comprises photographic paper and the characters are formed thereon by a photographic process.

6. A test card according to claim 5 further comprising a stiff, planar substrate fixed in parallel contact to the photographic paper.

7. A test card according to claim 1 wherein the dots within an individual pixel element are disposed along a plurality of substantially equally-spaced, concentric rings about the center of the array, adjacent dots along each ring having an angular spacing between them that is greater than an angular spacing between adjacent dots along a next adjacent ring closer to the center of the array, whereby the array has a maximum density of dots adjacent the center of the array and the dot density gradually decreases as a function of distance from the center.

8. A test card according to claim 1 wherein the test card includes an aperture extending therethough, the aperture sized and arranged so as to allow an examiner to view the patient's eyes generally along the patient's line of sight by looking through the test card from a side of the test card opposite the patient while the patient reads the characters on the test card.

9. A method of making an optometric test card comprising the steps of:

selecting a plurality of symbols for viewing by a patient; and forming an image comprising the selected symbols on a single, substantially opaque substrate for presentation to the patient; said forming step including forming each symbol of a plurality of pixel elements;

forming each pixel element of a plurality of dots;

within each pixel element, arranging the dots in a predetermined pattern having a maximum density of dots adjacent the center of the pattern, the dot density gradually decreasing as a function of distance from the center; and sizing the dots so that individual dots would not be discernable by a patient at a viewing distance greater than approximately 15 inches (38 cm.).

10. A method according to claim 9 wherein arranging the dots includes:

defining a concentric series of circles symmetrically disposed about the center of the pattern;

forming the dots so that each dot center lies on one of the circles;

spacing the dots along each circle apart by a predetermined angular spacing; and for each circle, selecting the angular spacing between adjacent dots so as to exceed a selected angular spacing between adjacent dots along a next adjacent circle closer to the center of the pattern, whereby the pattern has a maximum density of dots adjacent the center of the pattern and the dot density gradually decreases as a function of distance from the center.

11. A method according to claim 9 wherein arranging the dots includes:

designing a pattern of dots on a computer system having graphics software for representing the resulting pattern in a machine-readable graphics file;

providing the graphics file to a compatible imagesetter machine;

in the imagesetter machine, forming a pattern on photographic film in response to the graphics file;

duplicating the pattern by printing, the film on to photographic paper so as to produce a photographic print; and mounting the print onto a substrate to complete the test card.

* * * * *